US008780337B2

(12) United States Patent
Minneman et al.

(10) Patent No.: US 8,780,337 B2

(45) Date of Patent: Jul. 15, 2014

(54) SYSTEM AND METHOD FOR ELIMINATING THE EFFECT OF NON-PRIMARY LASER MODES ON CHARACTERIZATION OF OPTICAL COMPONENTS THROUGH CHARACTERIZED DECOMPOSITION

(75) Inventors: Michael Minneman, Lafayette, CO (US); Michael Crawford, Lafayette, CO (US)

(73) Assignee: Insight Photonic Solutions, Inc., Lafayette, CO (US)

( * ) Notice: Subject to any disclaimer, the term of this patent is extended or adjusted under 35 U.S.C. 154(b) by 32 days.

(21) Appl. No.: 13/555,106

(22) Filed: Jul. 21, 2012

(65) Prior Publication Data

US 2013/0044312 A1 Feb. 21, 2013

Related U.S. Application Data

(60) Provisional application No. 61/510,778, filed on Jul. 22, 2011.

(51) Int. Cl.

*G01N 21/00* (2006.01)
*G01N 21/31* (2006.01)
*G01N 21/33* (2006.01)

(52) U.S. Cl.

CPC .............. *G01N 21/314* (2013.01); *G01N 21/33* (2013.01)

USPC ............................................................ 356/51

(58) Field of Classification Search

CPC .................................................... G01N 21/314

USPC ............................................................ 356/51

See application file for complete search history.

(56) References Cited

U.S. PATENT DOCUMENTS 6,407,805 B1 * 6/2002 Sorin .......................... 356/73.1

* cited by examiner

*Primary Examiner* — Michael P Stafira

(74) *Attorney, Agent, or Firm* — Renner, Otto, Boisselle & Sklar, LLP

(57) ABSTRACT

A method and a system for characterization of optical components through characterized decomposition of an optical device includes: directing incident light over a range of wavelengths to a device under test, wherein the incident light includes a primary signal and at least one sideband signal, the distance between the primary signal and any one of the sideband signals is substantially larger than the width of the band pass area of the device under test; detecting output light from the device under test to obtain a detected signal; correcting the detected signal to account errors associated with the sideband signal.

24 Claims, 6 Drawing Sheets

SYSTEM AND METHOD FOR ELIMINATING THE EFFECT OF NON-PRIMARY LASER MODES ON CHARACTERIZATION OF OPTICAL COMPONENTS THROUGH CHARACTERIZED DECOMPOSITION

RELATED APPLICATION DATA

This application claims the benefit of U.S. Provisional Application No. 61/510,778, filed Jul. 22, 2011, which is hereby incorporated in by reference.

TECHNICAL FIELD

The present invention relates generally to a system and a method for eliminating the effect of non-primary laser modes on characterization of optical components through characterized decomposition.

BACKGROUND

Typically, an external cavity tunable laser source is used to characterize passive optical components. Generally, the tunable laser is swept across the wavelength of interest and the resulting signal change in power can be converted to insertion loss versus wavelength.

An external cavity laser can be made such that most of its power is in a single mode, with very small sideband signals. As such, the sideband signals are so small as to have an insignificant effect on the measurement of the passive optical component. Tunable lasers based on Vernier-tuned Bragg Reflector (VTDBR) monolithic tunable lasers are being developed. Such lasers may be referred to herein as Semiconductor Monolithic Tunable Laser Source (SMTLS). There are some advantages to these, including speed of the sweep and cost reduction over conventional lasers. However, the sideband signals are larger with SMTLS lasers, which can degrade the quality of the measurement. This degradation is due to the unwanted effects of the sideband signals.

SUMMARY

By utilizing the unique characteristic that the side-band spacing is substantially larger than the pass-band of the device under test (DUT), the undesired parasitic signal can be extracted from the correct characterization of the insertion loss of the device.

One aspect of the invention relates to a method for characterization of optical components through characterized decomposition of an optical device, the method including: directing incident light over a range of wavelengths to a device under test, wherein the incident light includes a primary signal and at least one sideband signal, the distance between the primary signal and any one of the sideband signals is substantially larger than the width of the band pass area of the device under test; detecting output light from the device under test to obtain a detected signal; and correcting the detected signal to account errors associated with the sideband signal.

Another aspect of the invention relates to an optical testing system, the system including: a semiconductor laser source configured to direct incident light over a range of wavelengths to a device under test, wherein the incident light includes a primary signal and at least one sideband signal, the distance between the primary signal and any one of the sideband signals is substantially larger than the width of the band pass area of the device under test; a detector configured to detect output light from the device under test to obtain a detected signal; one or more processors coupled to the detector, wherein the one or more processors are configured to correct the detected signal to account errors associated with the sideband signal and characterize the corrected signal; and a system output configured to output the characterized information of the device under test.

A number of features are described herein with respect to embodiments of the invention. It will be appreciated that features described with respect to a given embodiment also may be employed in connection with other embodiments.

The invention comprises the features described herein, including the description, the annexed drawings, and, if appended, the claims, which set forth in detail certain illustrative embodiments. These embodiments are indicative, however, of but a few of the various ways in which the principles of the invention may be employed.

DESCRIPTION

Figure 1:
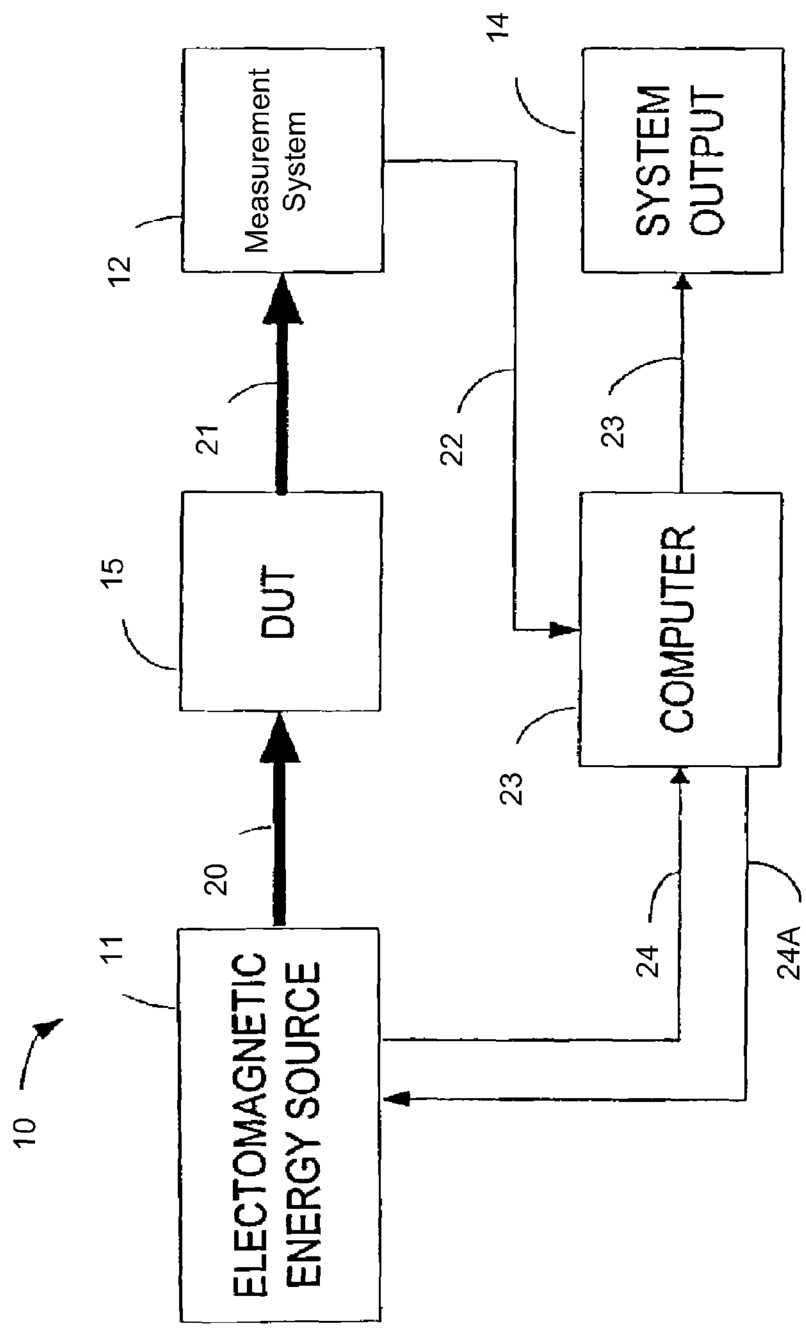
FIG. 1 illustrates an exemplary system in accordance with aspects of the present invention.

Referring to FIG. 1, an optical testing system 10 (also referred to as optical measurement system) is illustrated. The optical testing system 10 includes a semiconductor laser source 12, a detector 14, a processor 16, and a system output 20. A target object, referred to as a device under test (DUT) 18, is placed in the optical testing system 10, and in operation of the optical testing system 10, the DUT 18 may be characterized. In characterizing the DUT 18, incident light 22 is provided to the DUT 18. Output light 23 from the DUT 15 is detected by the detector 14 and may be used to characterize the optical characteristics of the DUT 18, as will be described further below. A person of ordinary skill in the art will appreciate that the DUT 18 may be an object, a subject, a portion of a subject, etc. An example of DUT 18 is a passive optical component, for example, an optical fiber cable.

During characterization of the DUT 18, the semiconductor laser source 12 is configured to receive an input signal 21 to discreetly change the radiation over the range of wavelengths (e.g., from a start wavelength to a stop wavelength).

Figure 2:
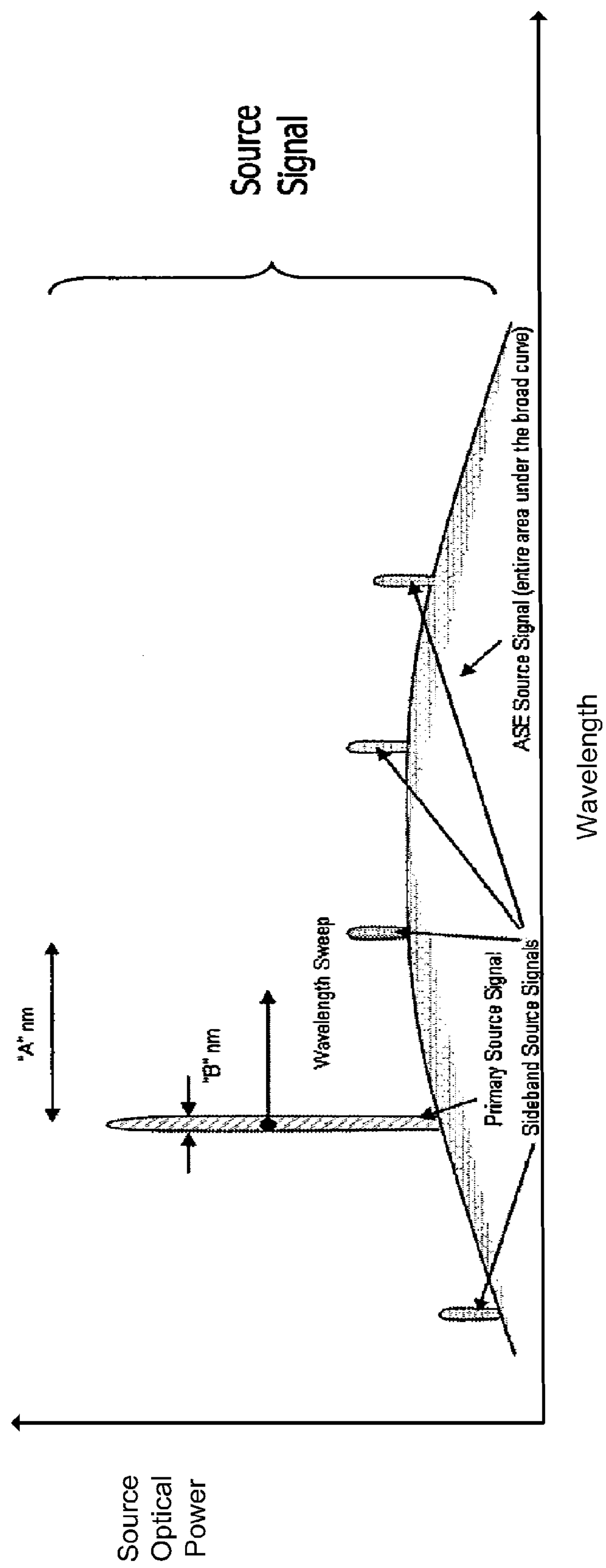
FIG. 2 illustrates an exemplary incident signal having a primary signal, sideband signals, and an ASE signal.
Figure 3:
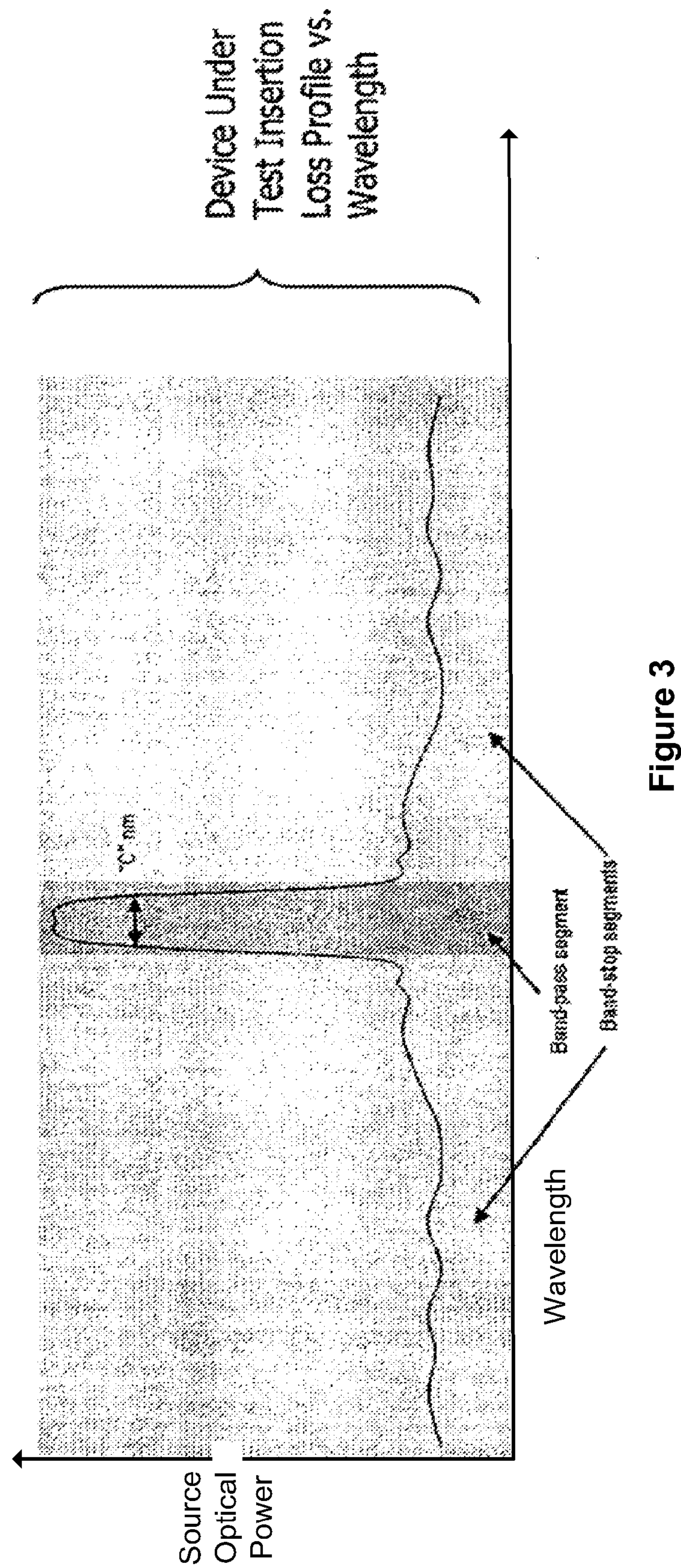
FIG. 3 illustrates an exemplary device under test insertion loss profile versus wavelength.

Referring to FIGS. 2 and 3, the incident light 22 (referred to as source signal), which may include a primary signal and one or more sideband signals, sweeps from lower wavelength (left) to higher wavelength (right). The primary signal and the sideband signals move together. The source signal 22 also includes an amplified spontaneous emission (ASE) signal, which is a type of light noise produced by spontaneous emission. The ASE signal remains constant versus wavelength. In one embodiment, the source signal may include a primary signal and a sideband signal. However, a person having skill in the art should understand that the present subject matter may be implemented with a source signal having a primary signal and plural sideband signals.

It also should be understood that the following assumptions are made as typical values with respect to the illustrative embodiments. A person having skill in the art will appreciate that the values presented below are exemplary in nature and not intended to limit the scope of the present invention.

The DUT:

The insertion loss of the band stop areas of the DUT: Ls=−40 dB;

The insertion loss of the pass band area of the DUT: Lp=−4 dB;

The width of the pass band area of the DUT (i.e. the filter width): C=0.4 nm;

The ASE Signal:

The power of the ASE signal: Pase=−45 dBm;

The width of the ASE signal: D=100 nm;

The Sideband Signal:

The power of sideband signal: Psb=−37 dBm.

The spacing between the primary signal and the sideband signal for an SGDBR:

A=5 nm;

The Primary Signal:

The power of the primary signal may be 0 dBm, for example.

The resulting signal of the DUT may be decomposed into six contribution sub-signals, as follows:

A first sub-signal, which is the resulting signal of the ASE signal passing through the band stop areas of the DUT;

A second sub-signal, which is the resulting signal of the ASE signal passing through the band pass area of the DUT;

A third sub-signal, which is the resulting signal of the sideband signal passing through the band stop areas of the DUT;

A fourth sub-signal, which is the resulting signal of the sideband signal passing through the band pass area of the DUT;

A fifth sub-signal, which is the resulting signal of the primary signal passing through the band stop areas of the DUT; and A sixth sub-signal, which is the resulting signal of the primary signal passing through the band pass area of the DUT.

The power of the first sub-signal equates to the power of the ASE signal times the insertion loss of the band stop areas of the DUT, i.e., The power of the first sub-signal=PASE*Ls=−85 dBm Thus, the first sub-signal is negligible.

The power of the second sub-signal equates to the filter width times the power of the ASE signal, times the insertion loss of the pass band area of the DUT, i.e., The power of the second sub-signal=C/D*PASE*Lp=−95 dBm Thus, the second sub-signal is negligible.

The power of the third sub-signal equates to the power of a sideband signal times the insertion loss of the band stop areas of the DUT, i.e.

The power of the third sub-signal=Psb*Ls=−37 dBm*(−40 dB)=−77 dBm Thus, the third sub-signal is negligible.

The power of the fourth sub-signal equates to the power of a sideband signal times the insertion loss of the band pass area of the DUT, e.g., the power of the fourth sub-signal=Psb*Lp=−37 dBm*(−4 dB)=−41 dBm. This resulting signal is the actual correct signal, which is Pp*Ls=0 dBm*−40=−40 dBm, for example. The −41 dBm error signal is appreciable compared to the −40 bBm nominal signal, creating a notable error.

Compared with the third sub-signal, the power of the fourth sub-signal may be significant. Therefore, the fourth sub-signal may be shown in the form of a bump. The bump in the apparent insertion loss of the device is the concatenation of the nominal actual insertion loss with the effect of the fourth subsignal through the passband of the device.

The power of the fifth sub-signal equates to the power of the primary signal times the insertion loss of the band stop areas of the DUT, e.g., the power of the fifth sub-signal=Pp*Ls=0 dBm*−40 dBm=−40 dBm.

The power of the sixth sub-signal equates to the power of the primary signal times the insertion loss of the band pass area of the DUT, e.g., the power of the sixth sub-signal=Pp*Lp=0 dBm*−4 dBm=−4 dBm.

It should be noted that for the sub-signals passing through the band pass area of the DUT, the only substantial contributor to the resulting signal of the DUT is the sixth sub-signal. Therefore, the magnitude and shape of the measured insertion loss will be accurately represented. The resulting signal may be used to determine the shape of the band pass area of the DUT. In addition, the magnitude of the sideband signal is also known (this will change as the laser sweeps across the band pass area of the DUT). Therefore, the width, shape, magnitude, and position of the fourth sub-signal may then be determined. Thus, the resulting signal shape can be reliably determined as if there were no side bands.

A person having skill in the art will understand that a suitable algorithm may be applied whenever the sideband spacing is wider than the width of the band pass area of the DUT. If the sideband spacing is narrower than the width of the band pass area of the DUT, there will be an overlap between the fourth sub-signal and the sixth sub-signal so that the resulting signal cannot be decomposed. Therefore, the error caused by the sideband signal cannot be eliminated. If there are more than one sideband signals, it is required that the distance between the primary signal and any one of the sideband signals is substantially larger than the width of the band pass area of the DUT.

An example of a semiconductor laser source 12 is a Semiconductor Monolithic Tunable Laser Source (SMTLS). A SMTLS 12 provides a laser beam (sometimes referred to as light but may be other radiation) 22 as incident radiation to the DUT 18. It will be appreciated that other types of semiconductor laser sources may be used and fall within the spirit and scope of the present invention. For convenience and brevity the radiation from the semiconductor laser source will be referred as a laser beam 22 or simply as a light or a light beam. The sweep of the SMTLS 12 may be very fast, thus allowing the detector 14 to be able to examine the power spectrum of light from a DUT 18 in a time frame that is in the second to microsecond (μs) range.

The term “swept”, as used herein, means that the SMTLS 12 provides its light output at a number of wavelengths over a range of wavelengths. For example, the semiconductor laser source 12 discreetly provides radiation over a range of wavelengths. That the wavelengths are “over” a range or “in” a range does not require that all wavelengths are used in the range, although use of all wavelengths may be possible, for example, if the optical testing system 10 can use and/or produce and detect, all wavelengths in the range.

The wavelength range may comprise the visible range of light or a part of the visible range. The wavelength range may also contain wavelengths in the ultraviolet and/or infrared range. The wavelength range may be a combination, part, or entirety of the visible light range, ultraviolet range, infrared range, or any other suitable range of wavelengths. An exemplary wavelength range is from about 1520 nm to about 1620 nm. One of ordinary skill in the art will readily appreciate that the invention may be used with other wavelengths and wavelength ranges.

In the optical testing system 10, the light 22 from the SMTLS 12 is incident on the DUT 18, and light 23 from the DUT 18, e.g., transmitted or reflected thereby, is sensed or detected by the detector 14. The detector 14 provides a detected signal 24 that is representative of the sensed or detected light 23 from the DUT 18. The detected signal 24 is associated with at least one physical property associated with the incident light 22 over the range of wavelengths. The detected signal 24 may be provided to the processor 16 (or to another processor or computational device), and/or to an amplification or other signal conditioning circuit (not shown).

The light 23 from the DUT 18 includes light that interacts with and light that does not interact with the DUT 18. Light that interacts with the DUT, e.g., may include light that is scattered, reflected, refracted, and/or is affected in any way by the DUT 18. Light that does not interact with the DUT 18, e.g., may include light that passes through the DUT 18 without interacting with the DUT 18.

A person of ordinary skill in the art will readily appreciate that the detector 14 is capable of measuring or quantifying light incident on the detector 14. The detector 14 may comprise, for example, an image sensor, CCD sensor, CMOS sensor, or any device capable of measuring or quantifying light incident on the detector.

In an exemplary optical testing system 10, the processor 16 received detected signal 24 from the detector 14. The processor 16 isolates the fourth sub-signal from the detected signal in order to get a corrected signal. The processor 16 then processes the corrected signal to obtain the characterized information of the DUT 18.

In another exemplary optical testing system 10, the processor 16 receives the detected signal 24 from the detector 14. The processor 16 determines the shape of the pass band area of the DUT according to the sixth sub-signal. The processor 16 then determines the shape of the fourth sub-signal according to the shape of the pass band area of the DUT. The processor 16 isolates the fourth sub-signal from the detected signal in order to get a corrected signal and processes the corrected signal into the characterized information of the DUT.

The resulting amplified, conditioned or otherwise adjusted signal on line 25 is provided via the system output 20. The system output 20 may include the mentioned and/or other amplification, signal conditioning, computational, control, etc. circuitry or may include other circuitry for the purpose of obtaining useful system output information and/or signal for characterizing the DUT 18.

In the exemplary optical testing system 10, the processor 16 coordinates operation of the SMTLS 12 with the signal on line 25 to the system output 20. Therefore, as the SMTLS 12 moves, scans, sweeps, etc. through the wavelengths of light it produces, the system output information is representative of characteristics of the DUT 18 as the DUT 18 receives incident light 22 at respective wavelengths. As one example, such coordination between the SMTLS 12 operation and the detector's output signal on line 24 may be achieved by a signal from the SMTLS 12 provided on line 21A to the processor 16, such that the processor 16 is "aware" of the wavelength or other characteristic of the light produced by the SMTLS 12.

As another example, the processor 16 may provide a control signal on line 21 to the SMTLS 12 to "direct" or to instruct the SMTLS 12 to produce a given light output. Coordination between the SMTLS 12 and processor 16 also may be based on time, whereby a timing signal may be used to indicate that the SMTLS 12 is starting (or is elsewhere in) its scan cycle or period; and based on known characteristics of the SMTLS 12, the wavelength of its output at subsequent can be accurately predicted. Other possibilities for such coordination also are possible.

A person of ordinary skill in the art will readily appreciate that a processor may be an ASIC, controller, computer, or any other type of device suitable for performing calculations and/or processing numbers. The functions processed by the processor 16 could be implemented by one or more processors. For example, one processor may implement the step of determining the shape of the pass band area of the DUT according to the sixth sub-signal. Another processor may implement the step of determining the shape of the fourth sub-signal according to the shape of the pass band area of the DUT. A third processor may isolate the fourth sub-signal from the detected signal in order to get a corrected signal. A fourth processor may process the corrected signal into the characterized information of the DUT. The above four processors may be coupled together in order to implement all the necessary functionality. A person of ordinary skill in the art will readily appreciate that a single processor and/or a combination of processors may be used to perform the functionality described herein.

Figure 4:
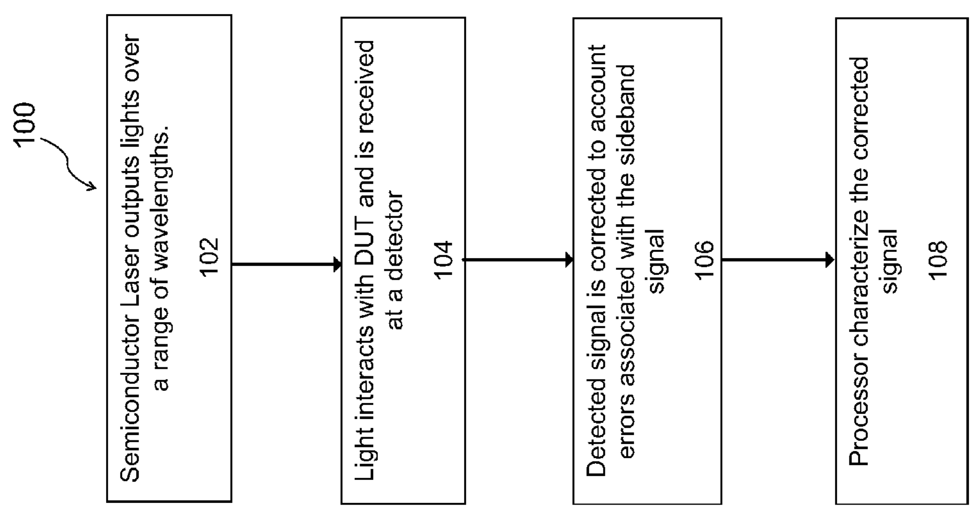
FIG. 4 illustrates an exemplary method in accordance with aspects of the present invention.

An exemplary method 100 for characterization of optical components through characterized decomposition is illustrated in FIG. 4.

At block 102, a semiconductor laser source outputs lights over a range of wavelengths. The radiation includes a primary signal and a sideband signal. The distance between the primary signal and the sideband signal is substantially larger than the band pass area of the device under test.

At block 104, the light interacts with and/or is transmitted by a DUT; and the light from the DUT is received by a detector.

At block 106, the detected signal from the detector is provided to a processor and the processor corrects the detected signal to account errors associated with the sideband signal.

At block 108, the processor may characterize the corrected signal when testing a DUT and/or optical components, for example.

Figure 5:
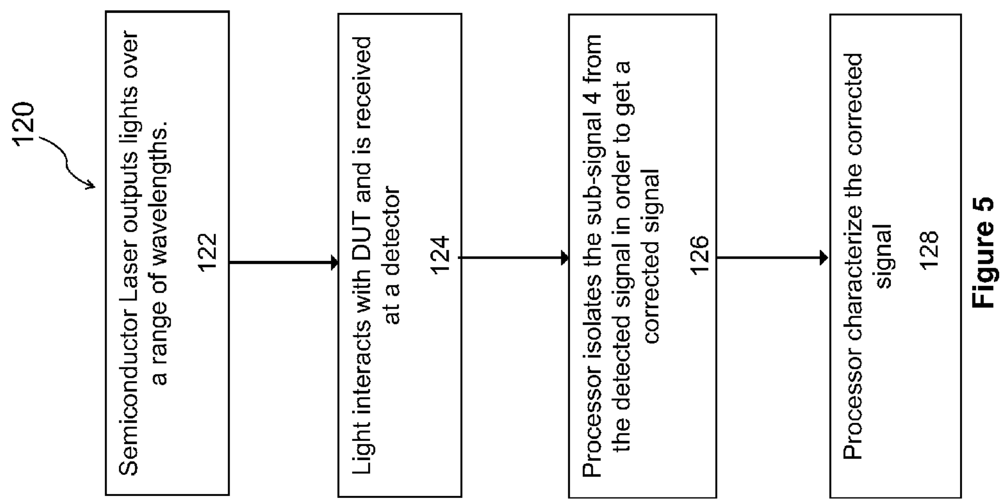
FIG. 5 illustrates another exemplary method in accordance with aspects of the present invention.

Another exemplary method 120 for characterization of optical components through characterized decomposition is illustrated in FIG. 5.

At block 122, a semiconductor laser source outputs lights over a range of wavelengths. The radiation includes a primary signal and a sideband signal. The distance between the primary signal and the sideband signal is substantially larger than the band pass area of the device under test.

At block 124, the light interacts with and/or is transmitted by a DUT; and the light from the DUT is received by a detector.

At block 126, the detected signal from the detector is provided to a processor and the processor isolates the sub-signal 4 from the detected signal in order to get a corrected signal. The sub-signal 4 is the resulting signal of the sideband signal passing through the band pass area of the DUT.

At block 128, the processor may characterize the corrected signal when testing a DUT and/or optical components, for example.

Figure 6:
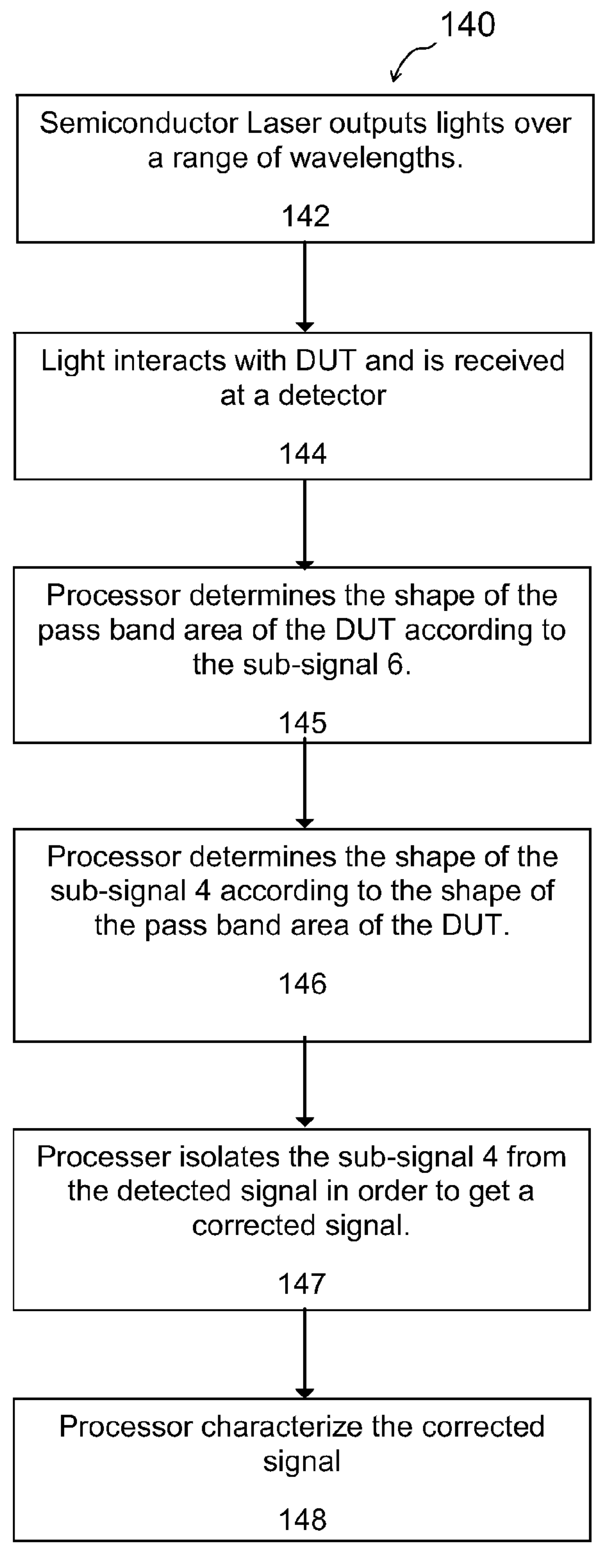
FIG. 6 illustrates another exemplary method in accordance with aspects of the present invention.

Another exemplary method 140 for characterization of optical components through characterized decomposition is illustrated in FIG. 6.

At block 142, a semiconductor laser source outputs lights over a range of wavelengths. The radiation includes a primary signal and a sideband signal. The distance between the primary signal and the sideband signal is substantially larger than the band pass area of the device under test.

At block 144, the light interacts with and/or is transmitted by a DUT; and the light from the DUT is received by a detector.

At block 145, the detected signal from the detector is provided to a processor. The processor determines the shape and width of the pass band area of the DUT according to the sub-signal 6. The sub-signal 6 is the resulting signal of the primary signal passing through the band pass area of the DUT.

At block 146, the processor determines the shape (e.g., width, magnitude, position) of the sub-signal 4 according to the shape of the pass band area of the DUT. The sub-signal is the resulting signal of the sideband signal passing through the band pass area of the DUT.

At block 147, the processor isolates the sub-signal 4 from the detected signal in order to get a corrected signal.

At block 148, the processor may characterize the corrected signal when testing a DUT and/or optical components, for example.

Although the invention is shown and described with respect to illustrative embodiments, it is evident that equivalents and modifications will occur to those persons skilled in the art upon the reading and understanding hereof. The present invention includes all such equivalents and modifications and is limited only by the scope of the claims if appended hereto.

What is claimed is:

1. A method for characterization of optical components through characterized decomposition of an optical device, the method comprising:

directing incident light over a range of wavelengths to a device under test, wherein the incident light includes a primary signal and at least one sideband signal, the distance between the primary signal and any one of the sideband signals is substantially larger than the width of the band pass area of the device under test;

detecting output light from the device under test to obtain a detected signal;

correcting the detected signal to account for errors associated with the sideband signal, wherein the correcting includes isolating a fourth sub-signal from the detected signal in order to get a corrected signal and the fourth sub-signal is the resulting signal of a first sideband signal of the at least one sideband signal passing through the band pass area of the device under test.

2. The method of claim 1, wherein the step of correcting the detected signal to account for errors associated with the sideband signal includes:

determining the shape of the pass band area of the device under test according to a sixth sub-signal, wherein the sixth sub-signal is the resulting signal of the primary signal passing through the band pass area of the device under test;

determining the shape of the fourth sub-signal according to the shape of the pass band area of the device under test; and isolating the fourth sub-signal from the detected signal in order to get a corrected signal.

3. The method of claim 1, wherein the incident light includes plural sideband signals and the plural sideband signals include the first sideband signal.

4. The method of claim 3, wherein the fourth sub-signal additionally includes the resulting signal of the plural sideband signals passing through the band pass area of the device under test.

5. The method of claim 3, wherein the step of correcting the detected signal to account for errors associated with the sideband signals includes:

determining the shape of the pass band area of the device under test according to a sixth sub-signal, wherein the sixth sub-signal is the resulting signal of the primary signal passing through the band pass area of the device under test;

determining the shape of the fourth sub-signal according to the shape of the pass band area of the device under test, wherein the fourth sub-signal additionally includes the resulting signal of the plural sideband signals passing through the band pass area of the device under test; and isolating the fourth sub-signal from the detected signal in order to get a corrected signal.

6. The method of claim 1, wherein the incident light is from a semiconductor tunable laser source.

7. The method of claim 6, wherein the semiconductor tunable laser is a Semiconductor Monolithic Tunable Laser.

8. The method of claim 7, wherein the Semiconductor Monolithic Tunable Laser is a Sampled Grating Distributed Bragg Reflector monolithic tunable laser.

9. The method of claim 1, wherein the device under test is a passive optical component.

10. The method of claim 9, wherein the passive optical component is an optical fiber cable.

11. The method of claim 1, wherein the range of wavelengths is from 1502 nm to 1604 nm.

12. The method of claim 1, wherein the distance between the primary signal and any one of the sideband signals is at least 5 nm larger than the width of the band pass area of the device under test.

13. An optical testing system, the system comprising:

a semiconductor laser source configured to direct incident light over a range of wavelengths to a device under test, wherein the incident light includes a primary signal and at least one sideband signal, the distance between the primary signal and any one of the sideband signals is substantially larger than the width of the band pass area of the device under test;

a detector configured to detect output light from the device under test to obtain a detected signal;

one or more processors coupled to the detector, wherein the one or more processors are configured to correct the detected signal to account for errors associated with the sideband signal and characterize the corrected signal, the correcting including isolating a fourth sub-signal from the detected signal in order to get a corrected signal, and the fourth sub-signal is the resulting signal of a first sideband signal of the at least one sideband signal passing through the band pass area of the device under test; and a system output configured to output the characterized information of the device under test.

14. The system of claim 13, wherein the one or more processors are configured to:

determine the shape of the pass band area of the device under test according to a sixth sub-signal, wherein the sixth sub-signal is the resulting signal of the primary signal passing through the band pass area of the device under test;

determine the shape of the fourth sub-signal according to the shape of the pass band area of the device under test; and isolate the fourth sub-signal from the detected signal in order to get a corrected signal.

15. The system of claim 13, wherein the incident light includes plural sideband signals and the plural sideband signals include the first sideband signal.

16. The system of claim 15, wherein the fourth sub-signal additionally includes the resulting signal of the plural sideband signals passing through the band pass area of the device under test.

17. The system of claim 15, wherein the one or more processors are configured to:

determine the shape of the pass band area of the device under test according to a sixth sub-signal, wherein the sixth sub-signal is the resulting signal of the primary signal passing through the band pass area of the device under test;

determine the shape of the fourth sub-signal according to the shape of the pass band area of the device under test, wherein the fourth sub-signal additionally includes the resulting signal of the plural sideband signals passing through the band pass area of the device under test; and isolate the fourth sub-signal from the detected signal in order to get a corrected signal.

18. The system of claim 13, wherein the incident light is from a semiconductor tunable laser source.

19. The system of claim 18, wherein the semiconductor tunable laser is a Semiconductor Monolithic Tunable Laser.

20. The system of claim 19, wherein the Semiconductor Monolithic Tunable Laser is a Sampled Grating Distributed Bragg Reflector monolithic tunable laser.

21. The system of claim 13, wherein the device under test is a passive optical component.

22. The system of claim 21, wherein the passive optical component is an optical fiber cable.

23. The system of claim 13, wherein the range of wavelengths is from 1502 nm to 1604 nm.

24. The system of claim 13, wherein the distance between the primary signal and any one of the sideband signals is at least 5 nm larger than the width of the band pass area of the device under test.

* * * * *